United States Patent
Kei et al.

(10) Patent No.: US 10,458,999 B2
(45) Date of Patent: Oct. 29, 2019

(54) CELL SUCTION SYSTEM, AND METHOD FOR PERFORMING SUCTION WORK OF INTRACELLULAR SUBSTANCE USING THE SAME

(71) Applicant: Yokogawa Electric Corporation, Musashino-shi, Tokyo (JP)

(72) Inventors: Takayuki Kei, Tokyo (JP); Takuya Azuma, Tokyo (JP); Hironori Takai, Tokyo (JP)

(73) Assignee: Yokogawa Electric Corporation, Musashino, Tokyo (JP)

( * ) Notice: Subject to any disclaimer, the term of this patent is extended or adjusted under 35 U.S.C. 154(b) by 180 days.

(21) Appl. No.: 14/959,160

(22) Filed: Dec. 4, 2015

(65) Prior Publication Data
US 2016/0169775 A1     Jun. 16, 2016

(30) Foreign Application Priority Data

Dec. 15, 2014   (JP) .................................. 2014-253164
Aug. 6, 2015    (JP) .................................. 2015-156437

(51) Int. Cl.
*G01N 35/10*     (2006.01)

(52) U.S. Cl.
CPC ................................. *G01N 35/1011* (2013.01)

(58) Field of Classification Search
CPC .................... G01N 1/14; G01N 2001/1031
See application file for complete search history.

(56) References Cited

U.S. PATENT DOCUMENTS

| | | | |
|---|---|---|---|
| 4,907,158 A | 3/1990 | Kettler et al. | |
| 5,631,165 A * | 5/1997 | Chupp et al. | B01F 5/0453 422/63 |
| 2005/0151092 A1 | 7/2005 | Kitagawa | |
| 2010/0317118 A1 | 12/2010 | Masujima et al. | |
| 2011/0124037 A1 | 5/2011 | Backhaus et al. | |

FOREIGN PATENT DOCUMENTS

| | | |
|---|---|---|
| EP | 1 744 194 A1 | 1/2007 |
| JP | 2007319038 A | 12/2007 |
| JP | 2010-504086 A | 2/2010 |
| JP | 5317983 B2 | 10/2013 |

* cited by examiner

*Primary Examiner* — Gautam Prakash
(74) *Attorney, Agent, or Firm* — Sughrue Mion, PLLC

(57) ABSTRACT

Provided is a cell suction system that supports suction work of a substance within a cell. The cell suction system includes: a suction section including a tubular tip configured to suction the substance from the inside of the cell received in a container; a detection section configured to acquire information on a front end part of the tip; and a conveyance section configured to make the suction section three-dimensionally movable, the conveyance section being configured to move the suction section to guide the front end part of the tip attached to the suction section into one specific cell based on the information obtained in the detection section.

22 Claims, 11 Drawing Sheets

CELL SUCTION SYSTEM, AND METHOD FOR PERFORMING SUCTION WORK OF INTRACELLULAR SUBSTANCE USING THE SAME

BACKGROUND OF THE INVENTION

Field of the Invention

The invention relates to a cell suction system that supports suction work of an intracellular substance, and a method for performing the suction work of the intracellular substance using the same. More particularly, the invention relates to a cell suction system and a method for performing suction work of an intracellular substance using the same that allow the position of suction means to be precisely controlled with respect to one target cell.

Priorities are claimed on Japanese Patent Application No. 2014-253164, filed Dec. 15, 2014, and Japanese Patent Application No. 2015-156437, filed Aug. 6, 2015, the contents of which are incorporated herein by reference.

Description of the Related Art

In recent years, drug discovery support devices have been developed which supply a compound which is a drug candidate to a cell, which is a basic constituent element of a living thing, analyze a change that takes place in the cell through image processing, and test the pharmacological effects and the side effects of the compound. In such drug discovery support devices, it is necessary to select a cell showing a noticeable unique change with respect to the compound, extract a substance within the cell (intracellular substance), set the substance on a mass spectrometer, and accurately analyze the substance.

For example, Japanese Patent No. 5317983 discloses a one-cell mass analysis method developed by Masujima, et al. In this method, a substance, such as an organelle, within a cell to be analyzed, is suctioned using an existing nanospray tip (glass capillary) while tracking changes in the cell with images of a microscope. Then, the mass of the suctioned substance is analyzed, and a molecular change is comprehensively analyzed. In this method, the work of determining a target cell to be analyzed and suctioning an organelle within the cell while visually confirming cells one by one is necessary. Therefore, this method is unsuitable to process a lot of cells. Additionally, when an organelle within a cell is suctioned, a user needs to find a front end of a suction tip by viewing. Therefore, this method requires improvements of working efficiency.

Additionally, Published Japanese Translation No. 2010-504086 of the PCT International Publication discloses a method of selecting a specific cell by imaging, sucking this selected cell, thereby proceeding to the following step, and culturing the cell. This method aims at suctioning a cell unit or suctioning a mass of a plurality of cells. As is also clear in this method, the positional precision of the suction tip is at the level of about tens of micrometers. Therefore, it is very difficult to precisely pick up a substance in a desired cell with such positional precision.

SUMMARY

The invention provides a cell suction system that supports suction work of an intracellular substance and allows the position of suction means to be precisely controlled with respect to one target cell.

A cell suction system supports suction work of a substance within a cell. The cell suction system includes: a suction section including a tubular tip configured to suction the substance from the inside of the cell received in a container; a detection section configured to acquire information on a front end part of the tip; and a conveyance section configured to make the suction section three-dimensionally movable, the conveyance section being configured to move the suction section to guide the front end part of the tip attached to the suction section into one specific cell based on the information obtained in the detection section.

The detection section may include: an optical input/output unit including a microscope having an objective lens and an imaging lens; and a signal-processing unit configured to be capable of introducing and removing an optical input signal and an optical output signal into and from a light path connecting the objective lens and the imaging lens. The suction section and the optical input/output unit may be configured such that the direction of the light path connecting the objective lens and the imaging lens and a longitudinal direction including the front end part of the tip maintain a parallel positional relationship.

The signal-processing unit may be arranged such that both of the optical input signal and the optical output signal are introduced into and removed from the light path connecting the objective lens and the imaging lens, through the imaging lens, further pass through the container, and reach the front end part of the tip.

The optical output signal may be image information on the front end part of the tip.

The signal-processing unit may be arranged such that both of the optical input signal and the optical output signal from the signal-processing unit are introduced into and removed from a portion in the middle of the light path connecting the objective lens and the imaging lens, further pass through the container, and reach the front end part of the tip.

The optical output signal may be reflective information on the front end part of the tip.

A light-receiving part that constitutes the signal-processing unit may be a confocal point optical type.

A light-receiving part that constitutes the signal-processing unit may be an astigmatic type.

A light-receiving part that constitutes the signal-processing unit may be a knife edge type.

A light-receiving part that constitutes the signal-processing unit may be an image contrast type.

A method for performing suction work of a substance within a cell using the above cell suction system includes: a step of causing the conveyance section to move the suction section to guide the front end part of the tip attached to the suction section to one specific cell based on the information obtained in the detection section.

The cell suction system of the invention includes a suction section including a tubular tip that suctions a substance from the inside of a cell received in a container; a detection section for acquiring information on a front end part of the tip; and a conveyance section that makes the suction section three-dimensionally movable. The conveyance section moves the suction section to guide the front end part of the tip attached to the suction section into one specific cell, based on the information obtained in the detection section. Accordingly, it is possible to provide a cell suction system that allows the position of suction means to be precisely controlled with respect to one target cell without depending on a worker's viewing. According to the invention, since it is possible to detect the front end position of the suction tip for sucking an intracellular substance, especially the position of the suction tip in a height direction with a micron order precision, a cell suction system with high flexibility according to one target cell can be constructed.

DETAILED DESCRIPTION OF THE PREFERRED EMBODIMENTS

In the following, a cell suction system and a method for performing suction work of an intracellular substance related to the preferred embodiment of the invention will be described with reference to the drawings.

First Preferred Embodiment

Light-Receiving Part that Constitutes Signal-Processing Unit is "Confocal Point Optical Type"

Figure 1:
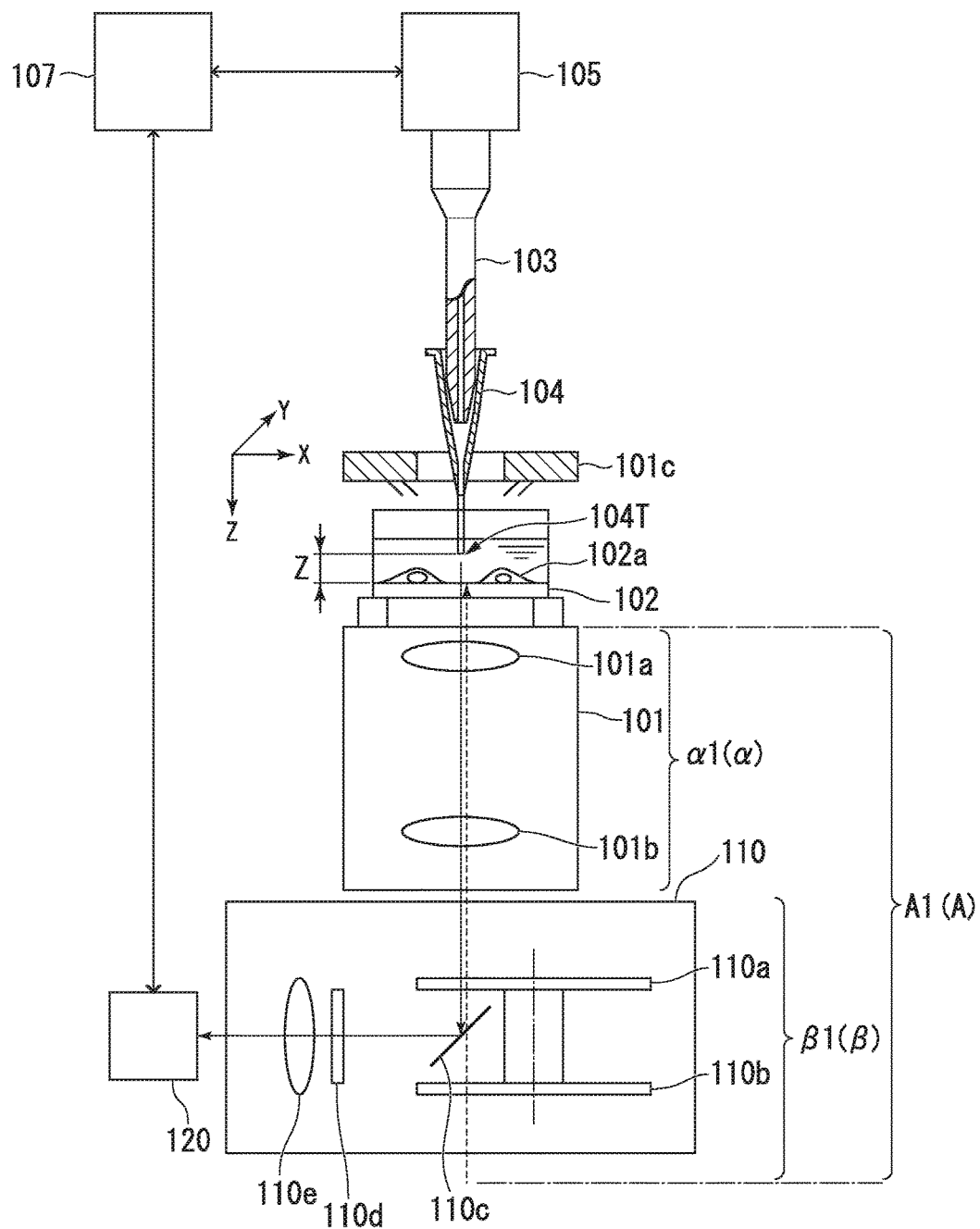
FIG. 1 is a view illustrating a configuration example of a cell suction system related to a first preferred embodiment of the invention.

FIG. 1 is a view illustrating a configuration example of a cell suction system related to a first preferred embodiment of the invention. The cell suction system illustrated in FIG. 1 supports suction work of an intracellular substance. However, the invention may be applied to a cell suction system that suctions one cell or a number of cells if necessary.

In the cell suction system illustrated in FIG. 1, a cell (sample) 102a and a culture solution are received in a container (sample holder) 102. The cell suction system includes a suction section 103 (dispenser) in which a front end that suctions an intracellular substance (mark O in the drawing) from the inside of the cell (sample) 102a received in the container (sample holder) 102 includes a tubular tip (suction tip) 104, a detection section A1(A) for acquiring information on a front end part 104T of the tip 104, and a conveyance section 105 that makes the suction section 103 three-dimensionally movable. When the conveyance section 105 moves the suction section 103 three-dimensionally based on the information obtained in the detection section A1(A), the front end part 104T of the tip 104 attached to the suction section 103 is guided into one specific cell.

In the above configuration, the detection section A1(A) includes an optical input/output unit $\alpha1(\alpha)$ consisting of a microscope 101 including an objective lens 101a and an imaging lens 101b; and a signal-processing unit $\beta1(\beta)$ configured to be capable of introducing and removing an optical input (transmission) signal (dotted line arrow in the drawing) and an optical output (reception) signal (solid line arrow in the drawing) into and from a light path connecting the objective lens 101a and the imaging lens 101b. Here, the dotted line arrow represents "a light beam with which a cell is illuminated", and the solid line arrow represents "a light beam reflected from the cell".

Additionally, in the above configuration, the suction section 103 and the optical input/output unit $\alpha1(\alpha)$ are configured such that the direction of the light path connecting the objective lens 101a and the imaging lens 101b and a longitudinal direction including the front end part 104T of the tip 104 maintain a parallel positional relationship. That is, in the cell suction system having the above configuration, the signal-processing unit $\beta1(\beta)$ is arranged such that both of the optical input (transmission) signal (dotted line arrow in the drawing) and the optical output (reception) signal (solid line arrow in the drawing) of the signal-processing unit $\beta1(\beta)$ are introduced into and removed from the light path connecting the objective lens 101a and the imaging lens 101b, through the imaging lens 101b, further pass through the container (sample holder) 102, and reach the front end part 104T of the tip 104. Accordingly, the output (reception) signal of the signal-processing unit $\beta1(\beta)$ is obtained as image information (photographs of image contrast) on the front end part 104T of the tip 104.

In the above configuration, the container (sample holder) 102 is arranged at a position on an extension line of an optical axis of the microscope 101, and a confocal microscope system is configured by providing the microscope 101 with a confocal point scanner 110 and a camera 120. Here, the confocal point scanner 110 is constituted of two array disks (a pinhole array disk 110a and a microlens array disk 110b) that are made rotatable on the same axis (one-dot chain line in the drawing), a dichroic mirror 110c, a band-pass filter 110d, and a relay lens 110e.

The suction section 103 (dispenser) is made movable in three illustrated XYZ directions by the conveyance section 105 in a state where the tip 104 is mounted on the front end of the suction section 103. The dispenser 103 is not particularly limited, and may be a commercially available type. The upward and downward operation (the operation in the Z direction) of the dispenser 103, the image processing of the camera, the control of the microscope, and the like are performed by the signal-processing unit 107.

Additionally, a light source 101c that illuminates the tip 104 may be provided in the microscope if necessary. The light source 101c is used as a light source when the tip 104 is illuminated and a bright-field image of a sample is acquired. By providing the light source 101c, since a state (a state where the quantity of reflected light becomes large) where the front end part 104T of the tip 104 shines can be further emphasized, visibility can be improved.

The type or arrangement of an illumination lamp used as the light source 101c can be freely set. A configuration in which the light source 101c is arranged so as to surround the tip 104 along the periphery of a side surface of the front end part 104T of the tip 104 is preferable. For example, a ring-shaped illumination lamp in which two or more LEDs are arrayed is most desirable as the above-described light source 101c. Accordingly, in photographs (FIG. 3) to be described, ring patterns of reflected light obtained when a focal point has coincided with the front end part 104T of the tip 104 can be clearly confirmed.

Figure 2:
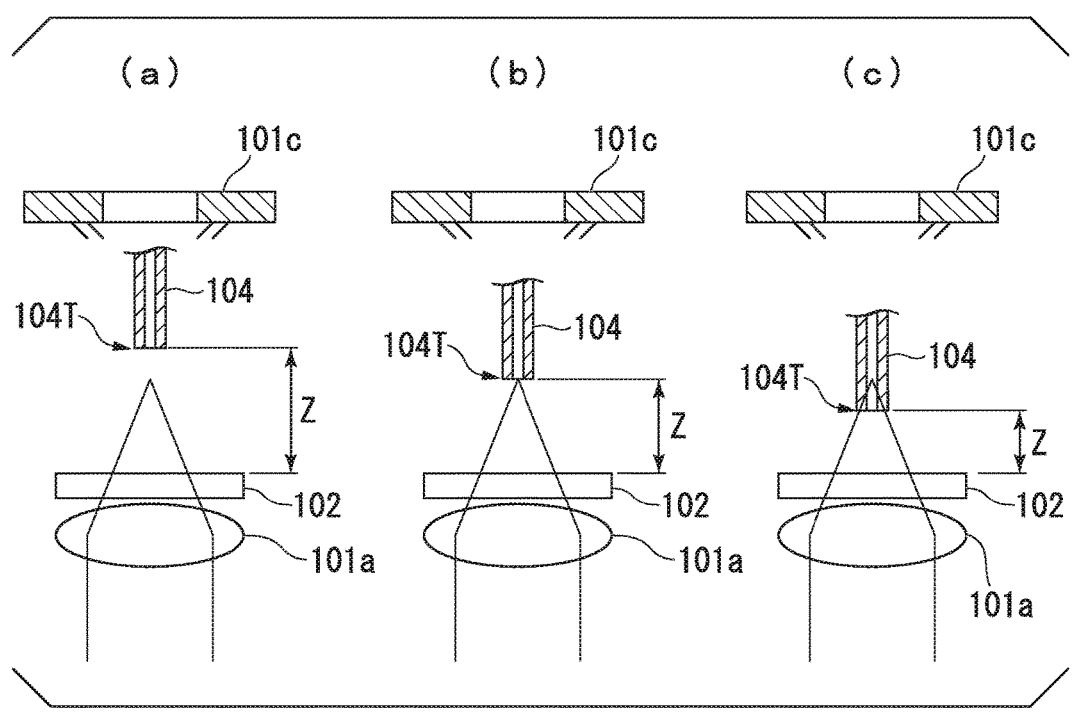
FIG. 2 is a view illustrating the principle of tip position measurement.
Figure 3:
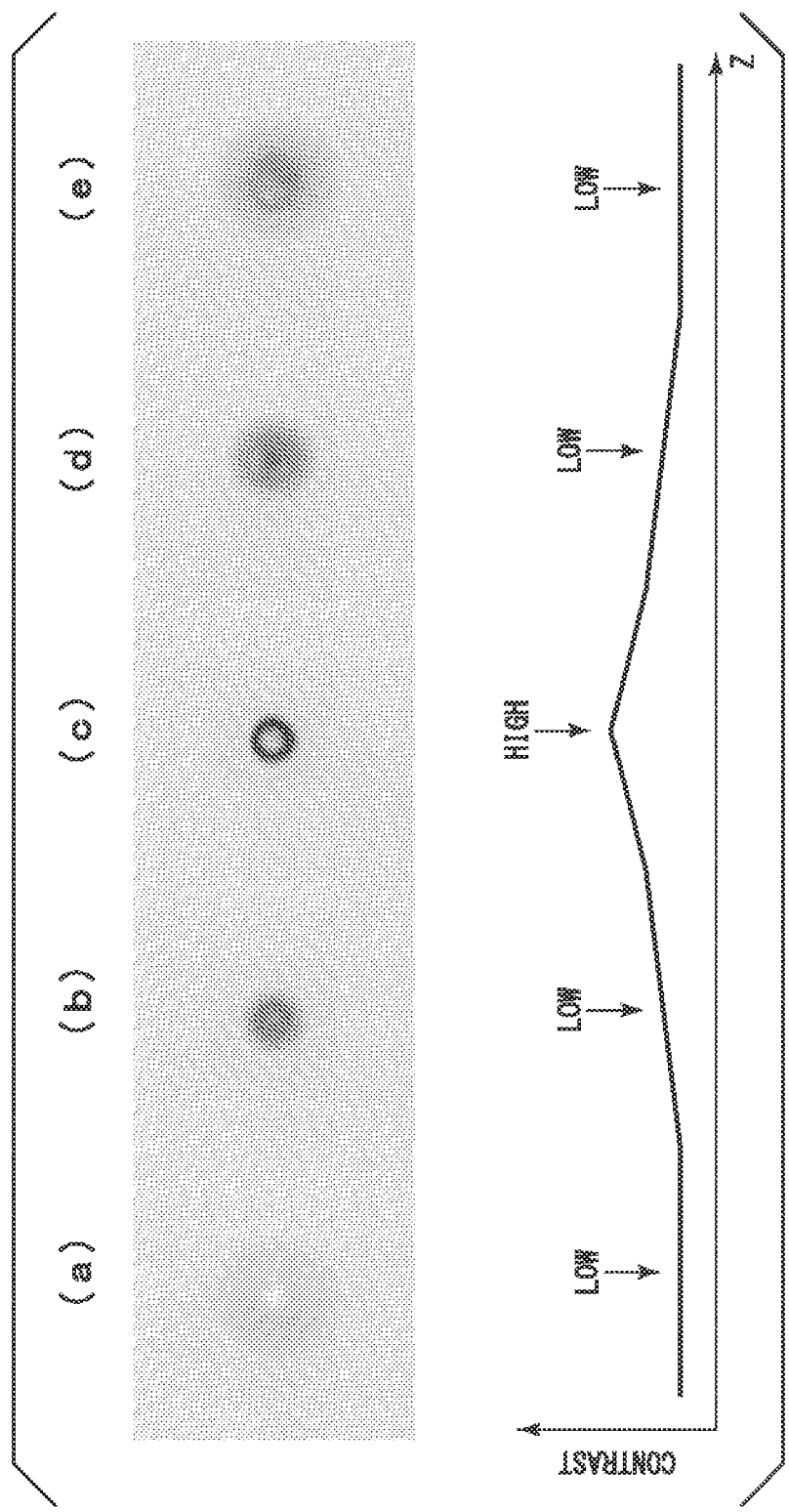
FIG. 3 is a view illustrating the relationship between images and tip positions that are observed based on FIGS. 1 and 2.

FIG. 2 is a view illustrating the principle of tip position measurement. FIG. 3 is a view illustrating the relationship between images and tip positions that are observed based on FIGS. 1 and 2. In the following, the detection principle (detection method) of the position of the front end part 104T of the suction tip 104 will be described with reference to FIGS. 2 and 3.

As illustrated in FIG. 2, the objective lens 101a is arranged at a height that is as close to the container (sample holder) 102 as possible. For example, the front end part 104T of the suction tip 104 is illuminated using the light source 101c consisting of the ring-shaped illumination lamp, and images of the front end part 104T are acquired by the confocal microscope system. If confocal point images are acquired while moving the suction tip 104 in the vertical direction (Z direction in FIGS. 1 and 2) ((a) to (c) of FIG. 2), images of the front end part 104T with different contrasts are obtained ((a) to (e) FIG. 3). When the front end part 104T of the suction tip 104 is located at the focal point of the objective lens 101a, an image of the highest contrast is obtained ((c) of FIG. 3). In this way, the position of the front end part 104T of the suction tip 104 is detected from the contrast of the image.

According to the above-described first preferred embodiment, the following working effects are obtained. Firstly, the position of the front end part 104T can be obtained as a value at the closest resolving power, that is, at a micron order by using a confocal point system for detection of the position of the front end part 104T of the suction tip 104. Secondly, by using the ring-shaped illumination lamp as the light source 101c, the vertical movement of the suction tip 104 becomes smooth, and reduction in cost of the device can be achieved. Thirdly, high-speed detection is possible by providing a configuration in which images are obtained using the confocal microscope having the pinhole array disks with a microlens.

Second Preferred Embodiment

Light-Receiving Part that Constitutes Signal-Processing Unit Ss "Confocal Point Optical Type"

Figure 4:
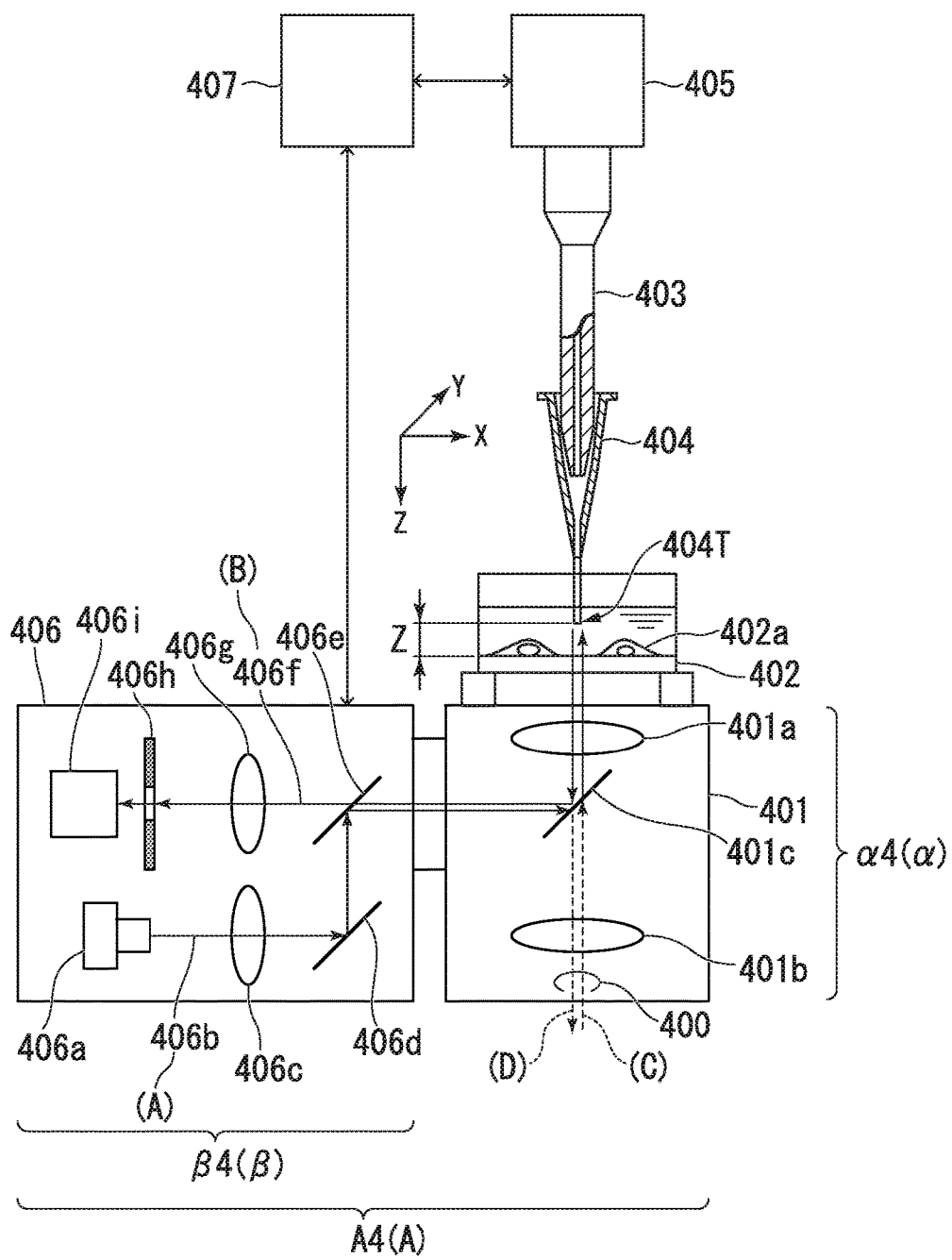
FIG. 4 is a view illustrating a configuration example of a cell suction system related to a second preferred embodiment of the invention.

FIG. 4 is a view illustrating a configuration example of a cell suction system related to a second preferred embodiment of the invention. The cell suction system illustrated in FIG. 4 supports suction work of an intracellular substance. However, the invention may be applied to a cell suction system that suctions one cell or a number of cells if necessary.

In the cell suction system illustrated in FIG. 4, a cell (sample) 402a and a culture solution are received in a container (sample holder) 402. The cell suction system includes a suction section 403 (dispenser) in which a front end that suctions an intracellular substance (mark O in the drawing) from the inside of the cell (sample) 402a received in the container (sample holder) 402 includes a tubular tip (suction tip) 404, a detection section A4(A) for acquiring information on a front end part 404T of the tip 404, and a conveyance section 405 that makes the suction section 403 three-dimensionally movable. When the conveyance section 405 moves the suction section 403 three-dimensionally based on the information obtained in the detection section A4(A), the front end part 404T of the tip 404 attached to the suction section 403 is guided into one specific cell.

In the above configuration, the detection section A4(A) includes an optical input/output unit α4(α) consisting of a microscope 401 including an objective lens 401a and an imaging lens 401b; and a signal-processing unit β4(β) configured to be capable of introducing and removing an optical input (transmission) signal (solid line arrow A in the drawing) and an output (reception) signal (solid line arrow B in the drawing) into and from a portion in the middle of a light path connecting the objective lens 401a and the imaging lens 401b. Here, a dotted line arrow C represents "a light beam with which a cell is illuminated", and a dotted line arrow D represents "a light beam reflected from the cell".

That is, in the cell suction system having the above configuration of FIG. 4, the signal-processing unit β4(β) is arranged such that both of the optical input (transmission) signal (solid line arrow A in the drawing) and the optical output (reception) signal (solid line arrow B in the drawing) from the signal-processing unit β4(β) are introduced into and removed from the portion in the middle of the light path connecting the objective lens 401a and the imaging lens 401b, further pass through the container (sample holder) 402, and reach the front end part 404T of the tip 404.

Additionally, in the above configuration, the suction section 403 and the optical input/output unit α4(α) are configured such that the direction of the light path connecting the objective lens 401a and the imaging lens 401b and a longitudinal direction including the front end part 404T of the tip 404 maintain a parallel positional relationship.

That is, in the cell suction system having the above configuration, the signal-processing unit β4(β) is arranged such that both of the optical input (transmission) signal (solid line arrow A in the drawing) and the optical output (reception) signal (solid line arrow B in the drawing) of the signal-processing unit β4(β) are introduced into and removed from the portion in the middle of the light path connecting the objective lens 401a and the imaging lens 401b, further pass through the container (sample holder) 402, and reach the front end part 404T of the tip 404. Accordingly, the output (reception) signal (solid line arrow B in the drawing) of the signal-processing unit β4(β) is obtained as information on the front end part 404T of the tip 404.

In the following, a case where the signal-processing unit β4(β) functioning as means (tip detecting unit) for detecting the position of the front end part 404T of the tip 404 will be described in detail. In the above configuration, a light source 406a is installed at a focal point of a lens 406c. Laser light (illumination light) 406b (solid line arrow A in the drawing) emitted from the light source 406a is collimated into parallel light by the lens 406c. The collimated parallel light enters a portion in the middle of the light path connecting the objective lens 401a and the imaging lens 401b that constitutes the microscope 401, through a mirror 406d and a beam splitter 406e, as irradiation light. Then, the irradiation light is reflected by a dichroic mirror 401c within the microscope 401, and irradiates the front end part 404T of the suction tip 404 via the objective lens 401a.

The illumination light that has reached the front end part 404T of the suction tip 404 is reflected by the front end part 404T, and advances in a direction opposite to the direction of the illumination light as reflected light 406f. The reflected light 406f (solid line arrow B in the drawing) is condensed by the objective lens 401a, and is reflected by the dichroic mirror 401c, is emitted from the microscope 401, and reaches the signal-processing unit β4(β) that functions as the tip detecting unit. The reflected light 406f (solid line arrow B in the drawing) that has reached the signal-processing unit β4(β) passes through the beam splitter 406e, and is condensed on a light-receiving sensor 406i by a condensing lens 406g. A confocal optical method is configured by providing a pinhole 406h at a focal position of the condensing lens 406g and allowing only the light at the focal point of the objective lens 401a to be transmitted therethrough. For example, when the light source 406a consisting of a laser diode with a wavelength of 780 nm, and a dichroic mirror 401c that reflects light of which spectral characteristics are a wavelength of 750 nm or more and transmits visible light not more than this wavelength therethrough is selected, a half mirror in which transmission pair reflection is 50:50 may be used as the beam splitter 406e.

The suction section 403 (dispenser) is made movable in three illustrated XYZ directions by the conveyance section 405 in a state where the tip 404 is mounted on the front end of the suction section 403. The dispenser 403 is not particularly limited, and may be a commercially available type. The upward and downward operation (the operation in the Z direction) of the dispenser 403, the image processing of the camera, the control of the microscope, and the like are performed by a signal-processing unit 407.

Figure 5:
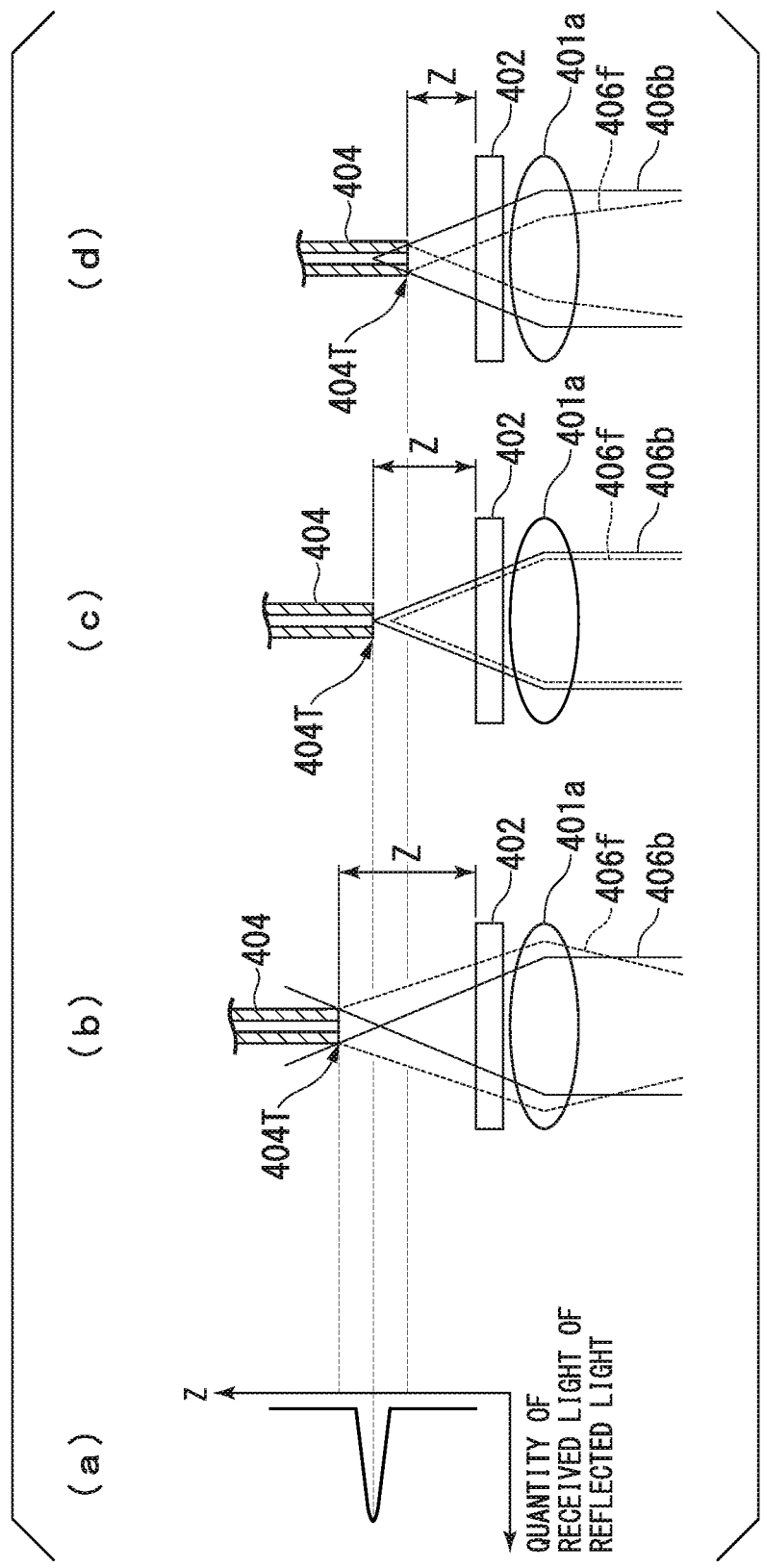
FIG. 5 is a view illustrating the relationship between the quantity of received light of reflected light and tip positions that are observed based on FIG. 4.

FIG. 5 is a view illustrating the principle of tip position measurement. (a) of FIG. 5 illustrates the quantity of received light of reflected light observed, and (b) to (d) of FIG. 5 illustrate the relationship between the quantity of received light of the reflected light and tip positions that are observed. In the following, the detection principle (detection method) of the position of the front end part 404T of the suction tip 404 will be described with reference to FIG. 5.

As illustrated in FIG. 5, the objective lens 401a is arranged at a height that is as close to the container (sample holder) 402 as possible. The front end part 404T of the suction tip 404 is illuminated using the laser light (illumination light) 406b, and the reflected light 406f from the front end part 404T is received by a light-receiving element. Since the suction tip 404 (front end part 404T) is made of glass, the reflectivity of light is very high. Thus, detection using reflected light is effective.

By providing a light-receiving system with the pinhole 406h, a confocal optical method is constituted of the light-receiving system and the objective lens 401a. By virtue of this configuration, only light at the focal point of the objective lens 401a is received. If the suction tip 404 is moved in the vertical direction (Z direction in FIGS. 4 and 5) after such a confocal point arrangement is adopted ((b) to (d) of FIG. 5), the strength (the quantity of received light of reflected light) of reflected light to be received varies ((a) of FIG. 5). When the front end part 404T of the suction tip 404 is located at the focal point of the objective lens 401a, almost all of the reflected light passes through the pinhole 406h and reaches the light-receiving sensor 406i. The highest quantity of received light is obtained at this time ((a) of FIG. 5). The position of the front end part 404T of the suction tip 404 is estimated from the maximum value of the light-receiving sensor 406i.

The control of the upward and downward operation of the suction section (dispenser) 403 and the signal processing of the light-receiving sensor 406i are performed by the signal-processing unit 407. In consideration of the fact that the front end part 404T of the suction tip 404 has a hollow shape, in actual design, an illumination light source is arranged so as to deviate to a front or rear position by a given distance from the position of the pinhole 406h. By adopting such an arrangement, illumination light can be slightly diffused and the front end part 404T of the suction tip 404 can be effectively illuminated.

In the above-described second preferred embodiment, the following working effects are obtained by detecting the front end position of the tip that suctions an intracellular substance utilizing the reflected light from the front end part 404T of the suction tip 404, and by realizing a detection system with a simple configuration including a drive system that moves the suction tip 404 upward and downward and a confocal optical system that receives reflected light. Firstly, the position of the front end part 404T can be obtained as a value at the closest resolving power, that is, at a micron order by using a confocal point system for detection of the position of the front end part 404T of the suction tip 404. Secondly, since automatic detection is performed, a skilled worker is made unnecessary, and throughput improves. That is, a system in which a high-precision prolonged operation is possible is obtained. Thirdly, since high-precision position detection is performed, a target intracellular part can be reliably suctioned.

Third Preferred Embodiment

Light-Receiving Part that Constitutes Signal-Processing Unit is "Astigmatic Type"

Figure 6:
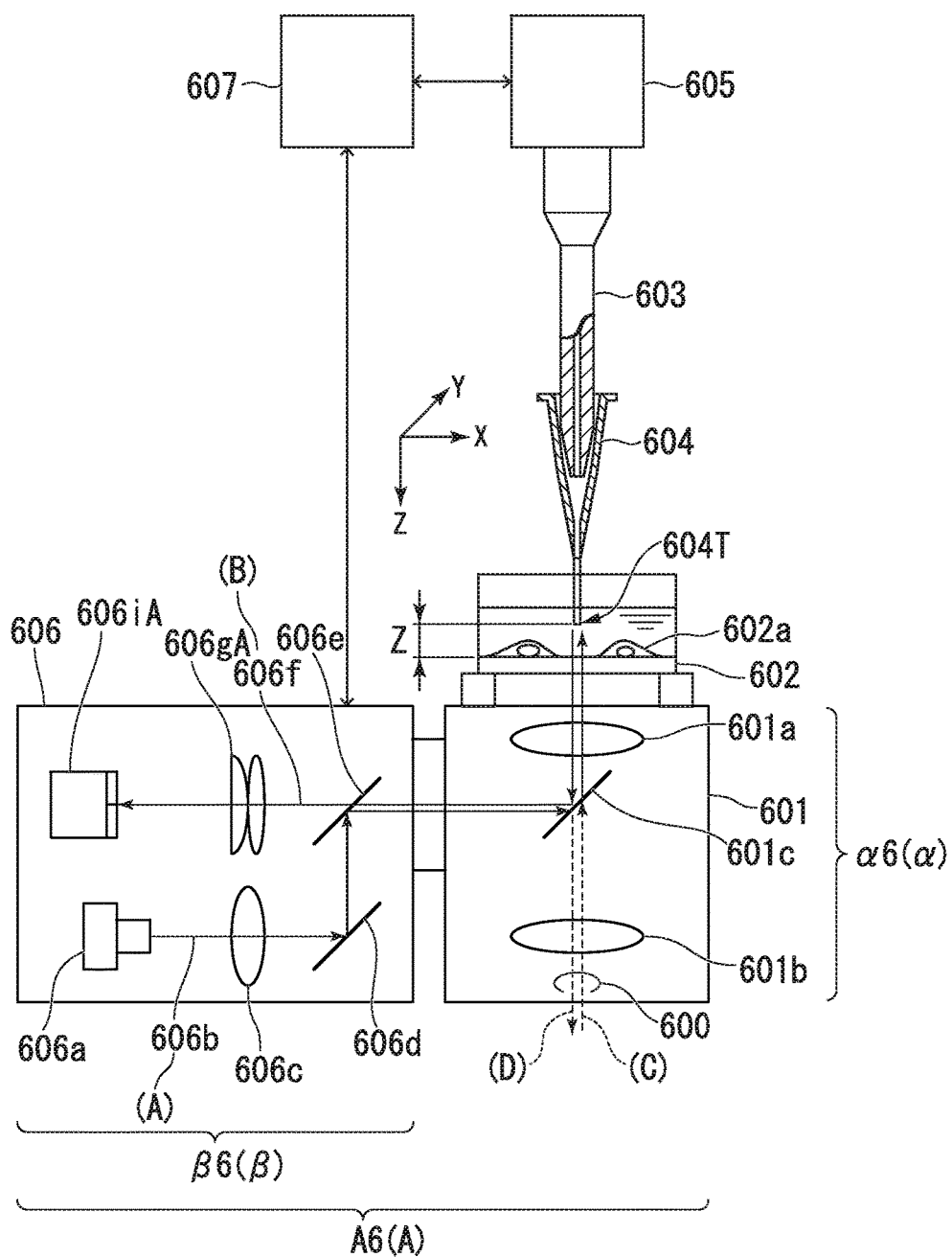
FIG. 6 is a view illustrating a configuration example of a cell suction system related to a third preferred embodiment of the invention.

FIG. 6 is a view illustrating a configuration example of a cell suction system related to a third preferred embodiment of the invention. The cell suction system illustrated in FIG. 6 supports suction work of an intracellular substance. However, the invention may be applied to a cell suction system that suctions one cell or a number of cells if necessary.

In the third preferred embodiment (FIG. 6), the light-receiving part is an astigmatic type, and a cylindrical lens 606gA is used instead of the condensing lens in the aforementioned second preferred embodiment (FIG. 4). A pinhole 406h in the second preferred embodiment (FIG. 4) is made unnecessary. A quadripartite PD (photodiode) is used as the light-receiving sensor 606iA. The other components are the same as those of the second preferred embodiment (FIG. 4). However, in order to be distinguished from the second preferred embodiment (FIG. 4), only reference numerals representing these respective components are in the 600s. The last two figures in reference numerals basically indicate the same structure as in FIGS. 4 and 6.

Figure 7:
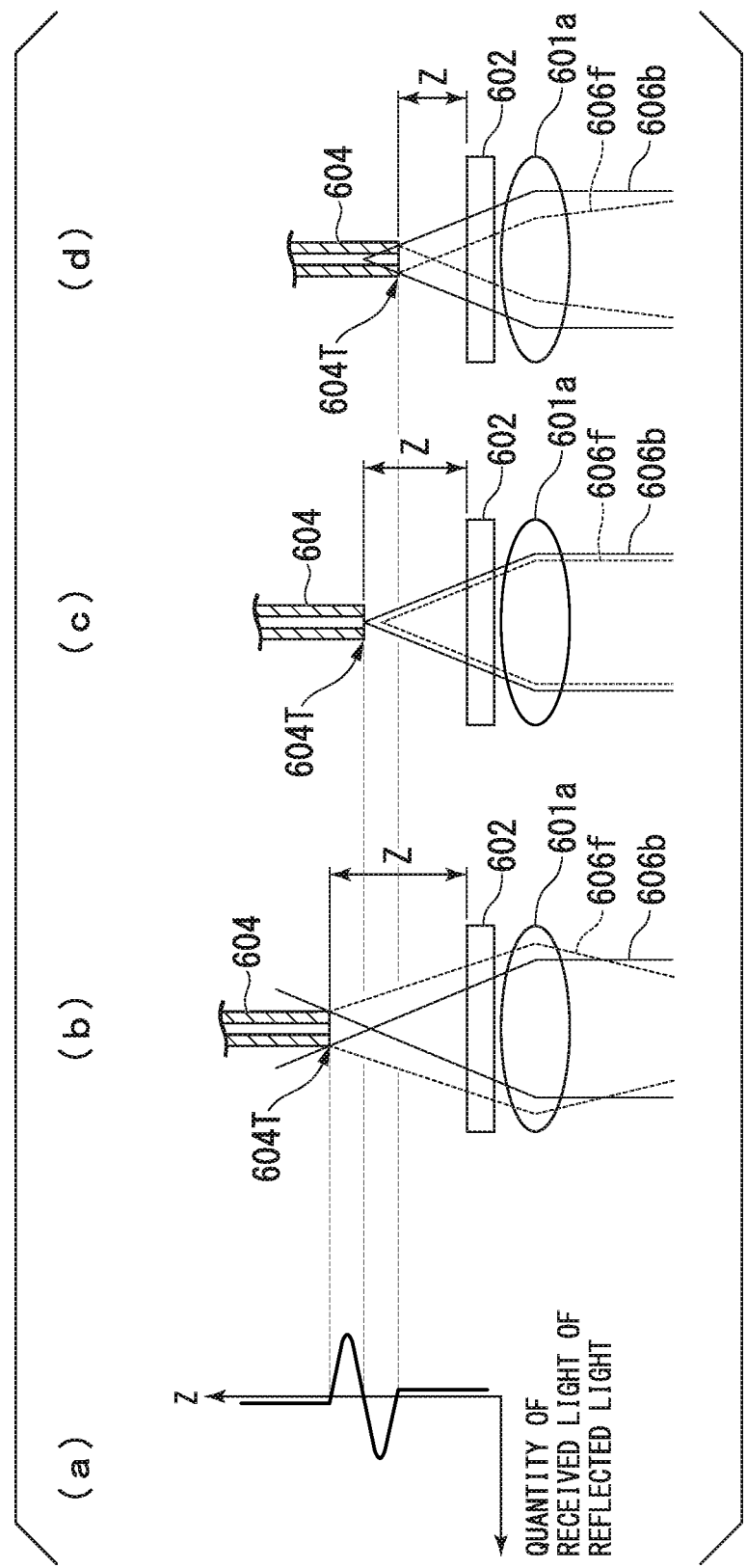
FIG. 7 is a view illustrating the relationship between the quantity of received light of reflected light and tip positions that are observed based on FIG. 6.

FIG. 7 is a view illustrating the principle of tip position measurement. (a) of FIG. 7 illustrates the quantity of received light of reflected light observed, and (b) to (d) of FIG. 7 illustrate the relationship between the quantity of received light of the reflected light and tip positions that are observed. In the following, the detection principle (detection method) of the position of a front end part 604T of a suction tip 604 when the light-receiving part is the astigmatic type will be described with reference to FIG. 7.

In the configuration of FIG. 7, when the suction tip 604 has been moved upward and downward ((b) to (d) of FIG. 7), the features (the features of the quantity of received light of reflected light) of signals of received light include cases where zero crossing points are present between the maximum (positive) and the minimum (negative). The zero crossing points appear when the front end part 604T of the suction tip 604 satisfies conditions in which the front end part is located at the focal point of the objective lens 601a. Therefore, in the configuration of the third preferred embodiment (FIG. 6), extremely accurate positional information (particularly the distance Z in the height direction) can be stably acquired by using information on the zero crossing points.

Fourth Preferred Embodiment

Light-Receiving Part that Constitutes Signal-Processing Unit is "Knife Edge Type"

A fourth preferred embodiment is an preferred embodiment in which the light-receiving part is a knife edge type, and is equivalent to a modification example of the aforementioned second preferred embodiment (FIG. 4). That is, in the fourth preferred embodiment, the light-receiving part is the knife edge type. The other components are the same as those of the second preferred embodiment (FIG. 4). In this method, a knife edge is provided instead of the pinhole 406h in the second preferred embodiment (FIG. 4). In that case, the knife edge is arranged on a focal plane of the condensing lens 406g. According to this configuration, almost the same reflected light signal as that of the aforementioned second preferred embodiment can be obtained. Therefore, also in the fourth preferred embodiment, it is possible to provide the cell suction system that brings about the same working effects as those of the second preferred embodiment.

Fifth Preferred Embodiment

Light-Receiving Part that Constitutes Signal-Processing Unit is "Image Contrast Type"

A fifth preferred embodiment is an preferred embodiment in which the light-receiving part is an image contrast type, and is equivalent to a modification example of the aforementioned second preferred embodiment (FIG. 4). In this method, a two-dimensional camera is arranged instead of the pinhole 406h in the second preferred embodiment (FIG. 4), and the photodiode that functions as the light-receiving sensor 606iA. Information consisting of an image of a front end part of a tip is acquired using a two-dimensional camera, and a place where the contrast of the image reaches the highest becomes the position of the front end part of the tip. By virtue of this configuration, the positional information on the front end part of the tip can be obtained substantially similarly to in the aforementioned second preferred embodiment. Therefore, also in the fifth preferred embodiment, it is possible to provide the cell suction system that brings about the same working effects as those of the second preferred embodiment.

Sixth Preferred Embodiment

High-Precision Position Measurement of Front End Part (Improvement of First Preferred Embodiment)

Figure 8:
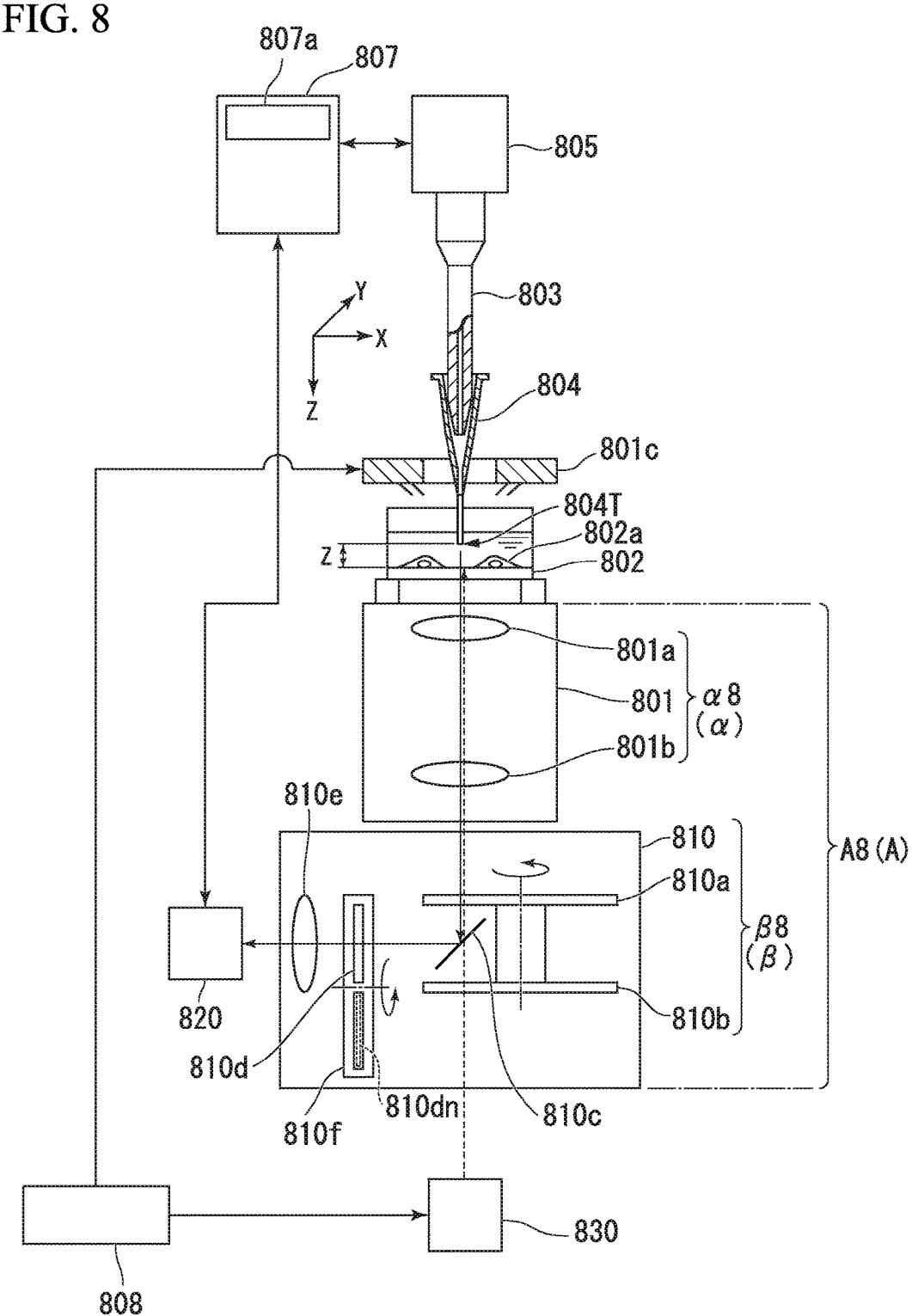
FIG. 8 is a view illustrating another configuration example of a cell suction system related to a sixth preferred embodiment of the invention.

FIG. 8 is a view illustrating a configuration example of a cell suction system related to a sixth preferred embodiment of the invention. The cell suction system illustrated in FIG. 8 supports suction work of an intracellular substance similar to the cell suction system of FIG. 1, and is equivalent to an improvement of the cell suction system (first preferred embodiment) of FIG. 1. However, the invention may be applied to a cell suction system that suctions one cell or a number of cells if necessary.

In the cell suction system illustrated in FIG. 1, when the position of the front end part 104T is measured, images of the front end part 104T are acquired using the light source 101c consisting of the ring-shaped illumination lamp. For example, examples of the images are the photographs of FIG. 3. As is clear from FIG. 3, also in the cell suction system of FIG. 1, the positional precision of the front end part 104T can be ensured to a level capable of supporting actual use. However, as illustrated in images (a photograph (a) and a photograph (e)) at both ends in FIG. 3, even if the front end part 104T is distant from the focal point of the objective lens 101a, blurring and fading may occur in the images. Therefore, the measurement precision of the front end position tends to decrease. A cell suction system (FIG. 8) to be described below in detail has been devised in order to solve such problems. This cell suction system aims to enable measurement (determination) of the position of the front end part with higher precision as compared to FIG. 3.

The cell suction system of FIG. 8 is based on the major components of FIG. 1 described above. The cell suction system of FIG. 8 is different from the cell suction system of FIG. 1 in that this cell suction system includes a filter wheel 810f, a light source control unit 808 that controls the ON/OFF state of a ring-shaped light source (illumination lamp) 801c and a light source 830 for confocal point observation, and a memory 807a within a signal-processing unit 807, in addition to the components of FIG. 1. Here, the filter wheel 810e is configured so that a plurality of bandpass filters 810d is mountable thereon, and one place 810dn of the mounting places does not have mounted thereon a bandpass filter, and functions as a "through position". In addition, in order to make the following description clear, the reference numerals in the 100s in FIG. 1 are changed to 800s and illustrated in FIG. 8. However, reference numerals of which the last two figures are the same basically indicate the same structures as in FIGS. 1 and 8.

In the cell suction system illustrated in FIG. 8, a cell (sample) 802a and a culture solution are received in a container (sample holder) 802. The cell suction system includes a suction section 803 (dispenser) in which a front end that suctions an intracellular substance (mark O in the drawing) from the inside of the cell (sample) 802a received in the container (sample holder) 802 includes a tubular tip (suction tip) 804, a detection section A8(A) for acquiring information on a front end part 804T of the tip 804, and a conveyance section 805 that makes the suction section 803 three-dimensionally movable. When the conveyance section 805 moves the suction section 803 three-dimensionally based on the information obtained in the detection section A8(A), the front end part 804T of the tip 804 attached to the suction section 803 is guided into one specific cell.

In the above configuration, the detection section A8(A) includes an optical input/output unit α8(α) consisting of a microscope 801 including an objective lens 801a and an imaging lens 801b; and a signal-processing unit β8(β) configured to be capable of introducing and removing an optical input (transmission) signal (dotted line arrow in the drawing) and an optical output (reception) signal (solid line arrow in the drawing) into and from a light path connecting the objective lens 801a and the imaging lens 801b. Here, the dotted line arrow represents "a light beam with which a cell is illuminated", and the solid line arrow represents "a light beam reflected from the cell".

Additionally, in the above configuration, the suction section 803 and the optical input/output unit α8(α) are configured such that the direction of the light path connecting the objective lens 801a and the imaging lens 801b and a longitudinal direction including the front end part 804T of the tip 804 maintain a parallel positional relationship. That is, in the cell suction system having the above configuration, the signal-processing unit β8(β) is arranged such that both of the optical input (transmission) signal (dotted line arrow in the drawing) and the optical output (reception) signal (solid line arrow in the drawing) of the signal-processing unit β8(β) are introduced into and removed from the light path connecting the objective lens 801a and the imaging lens 801b, through the imaging lens 801b, further pass through the container (sample holder) 802, and reach the front end part 804T of the tip 804. Accordingly, the output (reception) signal of the signal-processing unit β8(β) is obtained as image information (photographs of image contrast) on the front end part 804T of the tip 804.

In the above configuration, the container (sample holder) 802 is arranged at a position on an extension line of an optical axis of the microscope 801, and a confocal microscope system is configured by providing the microscope 801 with a confocal point scanner 810 and a camera 820. Here, the confocal point scanner 810 is constituted of two array disks (a pinhole array disk 810a and a microlens array disk 810) that are made rotatable on the same axis (one-dot chain line in the drawing), a dichroic mirror 810c, a bandpass filter 810d, and a filter wheel 810e.

Particularly, the sixth preferred embodiment is different from the first preferred embodiment in that the filter wheel 810f is used instead of the single bandpass filter 110d in the first preferred embodiment. The filter wheel 810f in the sixth preferred embodiment is configured such that a plurality of bandpass filters 810d is mountable thereon. Additionally, in the filter wheel 810f, one place 810dn among places where the plurality of bandpass filters 810d are made mountable functions as a so-called "through position" where no bandpass filter is mounted and a vacant hole (gap) is formed.

The suction section 803 (dispenser) is made movable in three illustrated XYZ directions by the conveyance section 805 in a state where the tip 804 is mounted on the front end of the suction section 803. The dispenser 803 is not particularly limited, and may be a commercially available type. The upward and downward operation (the operation in the Z direction) of the dispenser 803, the image processing of the camera, the control of the microscope, and the like are performed by the signal-processing unit 807.

In the sixth preferred embodiment, the light source 801c for when a bright-field image of a sample is acquired is included. However, unlike in the first preferred embodiment, in the sixth preferred embodiment, the light source 801c is not used in the front end position measurement of the front end part 804T of the tip 804, and the front end part 804 is instead illuminated with the illumination light from the light source 830 for confocal point observation. The illumination light reflected by the front end part 804T passes through the pinhole on the pinhole array disk 810a, a part thereof is reflected by the dichroic mirror 810c, and passes through the position 810dn of the filter wheel 810f, and an image is formed on the camera 820 by the relay lens 810e. That is, confocal point images of the front end part 804T are captured in the camera 820. Since light other than a focal plane of the objective lens 801a is removed by the pinhole on the pinhole array disk 810a, the confocal point images, as illustrated in the photographs (FIG. 11) to be described, are sharp optical tomographic images without blurring, and the visibility of the front end part 804T of the tip 804 improves. In the sixth preferred embodiment, the front end detection based on images with improved visibility is performed, and thereby, measurement is possible with higher precision at the position of the front end part as compared to the first preferred embodiment.

In the sixth preferred embodiment, the light source 801c that illuminates the tip 804 is necessarily provided in the microscope. The light source 801c is used as a light source when the tip 804 is illuminated, and a bright-field image of a sample is acquired. By providing the light source 801c, since a state (a state where the quantity of reflected light becomes large) where the front end part 804T of the tip 804 shines can be further emphasized, visibility can be improved. Particularly, in the sixth preferred embodiment, in order to arrange the light source 801c so as to surround the tip 804 along the periphery of the side surface of the front end part 804T of the tip 804, the ring-shaped illumination lamp in which a plurality of LEDs are arrayed is adopted as the light source 801c. Accordingly, in the photographs (FIG. 11) to be described, ring patterns of reflected light obtained when a focal point has coincided with the front end part 804T of the tip 804 can be clearly confirmed.

Figure 9:
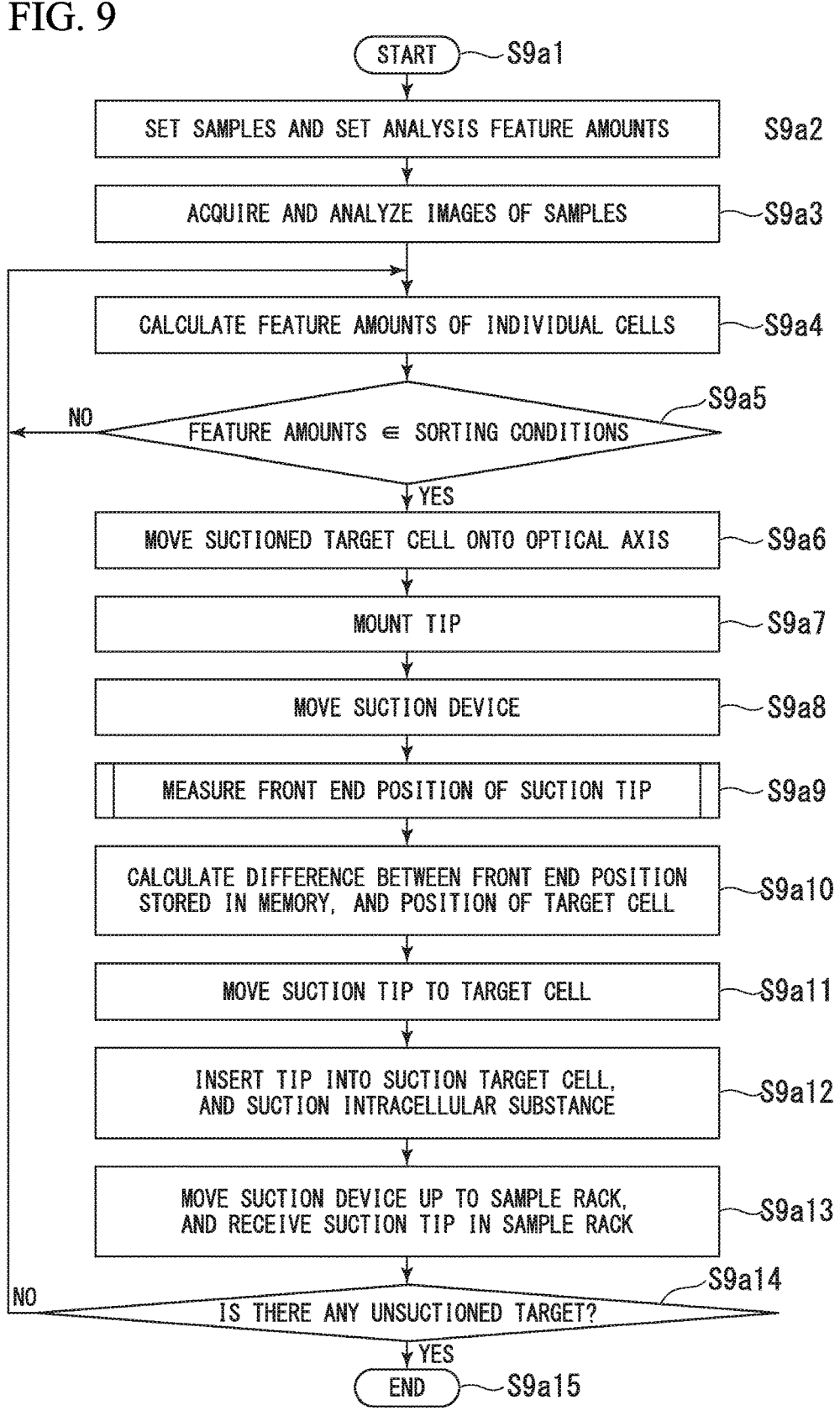
FIG. 9 is a flowchart explaining an operation using the cell suction system of FIG. 8.
Figure 10:
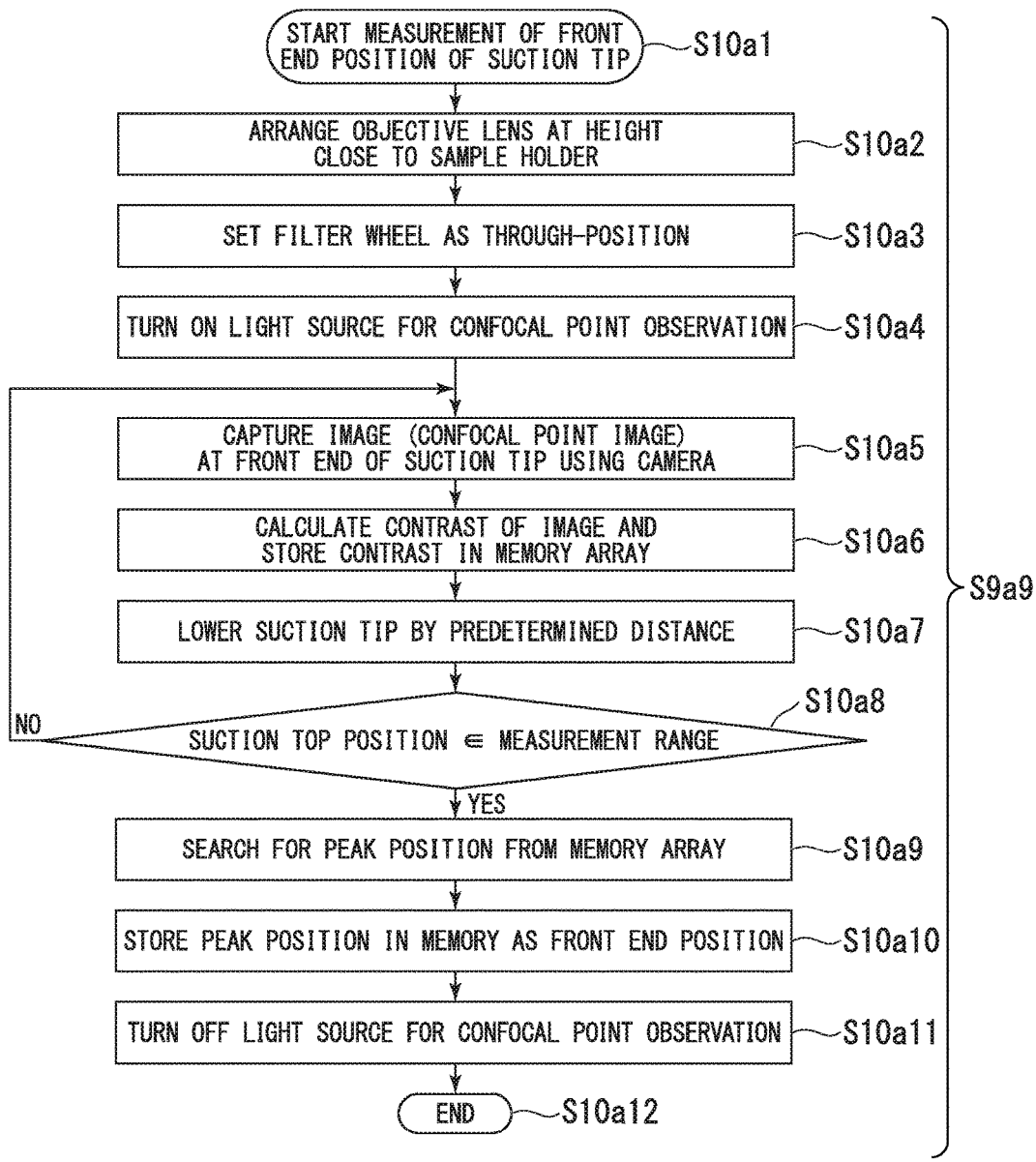
FIG. 10 is a flowchart explaining some steps (front end position measurement of a tip) of FIG. 9.
Figure 11:
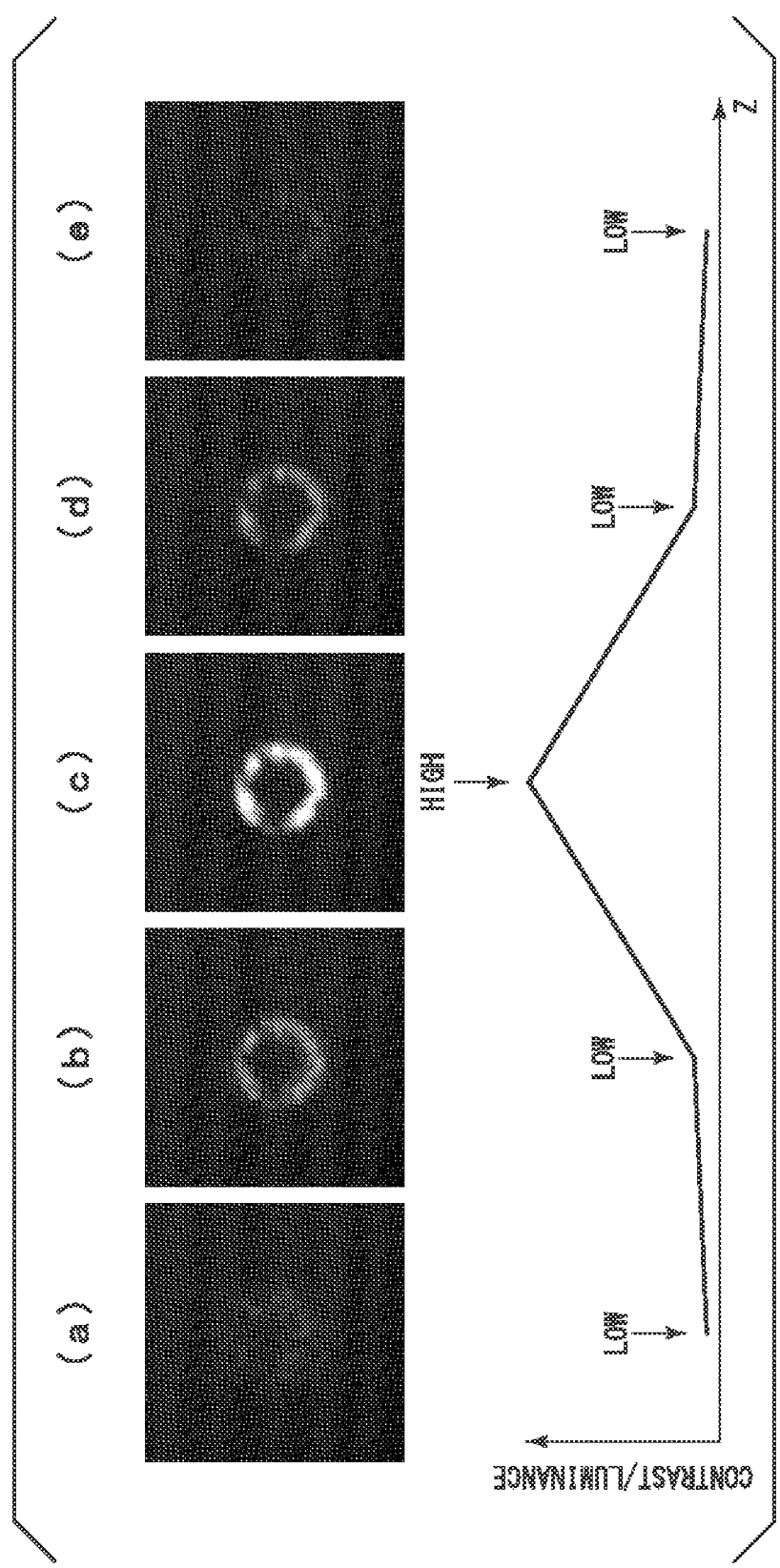
FIG. 11 is a view illustrating the relationship between images and tip positions that are observed based on FIGS. 8 to 10.

FIG. 9 is a flowchart explaining an operation using the cell suction system of FIG. 8, and FIG. 10 is a flowchart explaining some steps (front end position measurement of the tip) of FIG. 9. FIG. 11 is a view illustrating the relationship between images and tip positions that are observed based on FIGS. 8 to 10. In the following, the detection principle (detection method) of the position of the front end part 804T of the suction tip 804 will be described with reference to FIGS. 9 and 10.

(Step S9a2) A user sets the container (sample holder) 802 containing cells in a device.

(Step S9a2) The user sets the conditions of the analysis feature amounts of cells to be suctioned in a system, and instructs the system to start suction.

(Step S9a3) The system acquires images of the samples and analyzes the images.

(Step S9a4) The feature amounts of the individual cells are calculated based on the analysis results of Step S9a3.

(Step S9a5) With respect to the individual cells, the processing proceeds to the suction processing after S9a6 only when the feature amounts of the cells satisfy fixed sorting conditions.

(Step S9a6) The system moves a suction target cell, which has satisfied the feature amount conditions, onto the optical axis of the objective lens 801a.

(Step S9a7) The system mounts a new suction tip 804 on the suction section 803.

(Step S9a8) Thereafter, the suction section 803 is moved to the suction target cell.

(Step S9a9) The system executes "front end position measurement processing" of the suction tip, and stores the front end position coordinates of the suction tip in the memory 807a. In addition, the "front end position measurement processing" of Step S9a9 will be described in detail in a subsequent stage with reference to FIG. 10.

(Step S9a10) The system calculates a difference between the front end position coordinates of the suction tip stored in the memory 807a, and the coordinates of the suction target cell.

(Step S9a11) The suction tip front end is brought close to the target cell when the suction section 803 is moved by the difference calculated in Step S9a10.

(Step S9a12) The system inserts the front end of the suction tip into the suction target cell, and suctions an intracellular substance.

(Step S9a13) The system moves the suction section 803 to a sample rack (not illustrated), and receives the suction tip 804, into which the suctioned sample has been put, into the sample rack.

(Step S9a14) The procedure of Step S9a4 to Step S9a13 is repeated until the cells that satisfy the sorting conditions are eliminated from the container 802.

In the following, the "front end position measurement processing" of the above-described Step S9a9 will be described in detail with reference to FIG. 10.

(Step S10a2) The system arranges the objective lens 801a at a height that is as close to the container (sample holder) 802 as possible.

(Step S10a3) The system sets the filter wheel 810f at the through position 810dn on which no bandpass filter 810d is mounted.

(Step S10a4) The system switches off the ring-shaped light source (illumination lamp) 801c using the light source control unit 808. Further, the light source 830 for confocal point observation is turned on. Accordingly, the front end part 804T of the suction tip 804 is irradiated with the illumination light (dotted line arrow of FIG. 8) when observing the confocal point images of the samples 802a.

(Step S10a5) The reflected light (the solid line arrow of FIG. 8) from the front end part 804T, that is, the confocal point image of the front end part 804T, is captured by the confocal microscope system.

(Step S10a6) The system calculates the contrast of the captured image, and records the front end position coordinates of the suction tip and the value of the contrast in the memory array.

(Step S10a7) The system lowers the suction tip 804 in the direction of the sample 802a by only a predetermined distance.

(Step S10a8) The system repeats the procedure of Step S10a5 to Step S10a7 until the position of the suction tip after the lowering is out of a fixed measuring range.

Through the above procedure, a series of images with different contrasts depending on the position of the suction tip are captured as illustrated in (a) to (e) of FIG. 11. In that case, the contrasts of the respective images are recorded on the array on the memory 807a together with the position coordinates of the suction tip.

(Step S10a9) The system searches for a peak value among a series of contrast values on the memory array.

(Step S10a10) The position coordinates of the suction tip corresponding to the peak value are recorded on the memory 807a. When the front end part 804T is located at the focal point of the objective lens 801a, the highest contrast is obtained ((c) of FIG. 11). By this operation, the position of the front end part 804T of the suction tip with respect to the objective lens 801a is obtained.

(Step S10a11) The system switches off the light source 830 for confocal point observation.

According to the above-described sixth preferred embodiment, the following working effects are obtained. Firstly, when the reflected light (the solid line arrow of FIG. 8) of the front end part 804T of the suction tip 804 passes through the pinhole array disk 810a, components from other than the focal plane of the objective lens 801a are removed. Therefore, with respect to the confocal point images of the front end part 804T captured by the confocal microscope system, when the front end part 804T is located at the focal plane of the objective lens 801a, the highest contrast is obtained. As a result, as the front end part moves out of the focal plane, the images become rapidly blurred, and fading disappears. That is, when the front end part moves out of the focal plane, the contrast decreases rapidly. Thus, the timing at which front end part 804T is located at the focal plane of the objective lens 801a can be clearly found.

The method for performing suction work of an intracellular substance using the cell suction system described in any one of the above-described first to sixth preferred embodiments includes a step in which the conveyance section moves the suction section based on the information obtained in the detection section, and the front end part of the tip attached to the suction section is guided to one specific cell.

Although the cell suction system and the method for performing suction work of an intracellular substance using this method, related to the invention, have been described above, the invention is not limited to this, and can be appropriately changed without departing from the scope of the invention.

For example, the invention makes it possible to suction an intracellular substance that produces a substance serving as a main raw material, such as a medical product, to utilize the intracellular substance. Therefore, the invention contributes to development of a medical product or the like. However, the invention is not limited to a medical product, and can be widely applied.

While preferred embodiments of the invention have been described and illustrated above, it should be understood that these are exemplary of the invention and are not to be considered as limiting. Additions, omissions, substitutions, and other modifications can be made without departing from the scope of the present invention. Accordingly, the invention is not to be considered as being limited by the foregoing description, and is only limited by the scope of the appended claims.

What is claimed is:

1. A cell suction system that supports suction work of a substance within a cell, the cell suction system comprising:
 a container configured to receive the cell;
 a tubular tip configured to suction the substance from the inside of the cell received in the container;
 an illumination lamp in which two or more light emitting elements are arrayed to surround the tubular tip;
 a microscope having an objective lens and an imaging lens, the objective lens being arranged below the container and at a height that is as close to the container; and
 a detection section configured to detect a position of a front end part of the tubular tip, the detection section comprising:
  an optical component assembly comprising:
   a pinhole array disk comprising a plurality of pinholes and configured to rotate:
   a dichroic mirror configured to reflect at least a portion of light having passed through the objective lens and the pinhole array disk and entering into the dichroic mirror; and
   a camera configured to detect the light reflected by the dichroic mirror,
  the optical component assembly being configured to acquire an optical output signal of the front end part of the tubular tip from a light path connecting the objective lens and the imaging lens;
  at least one memory storing instructions; and
  at least one processor coupled to the optical component assembly and programmed to execute the instructions to detect the position of the front end part of the tubular tip based on an optical output signal of the front end part of the tubular tip acquired from a light path connecting the objective lens and the imaging lens,
 wherein a direction of an optical axis of the objective lens and a longitudinal direction including the front end part of the tubular tip are parallel, and
 wherein the processor is programmed to execute the instructions to detect a position in a height direction where the front end part of the tubular tip is located at a focal point of the objective lens based on variation of the output signal when the front end part of the tubular tip is moved in the longitudinal direction, and
 wherein the processor determines that the front end part of the tubular tip is located at the focal point of the objective lens when a contrast of the front end part of the tubular tip is high in the optical output signal of the front end part of the tubular tip.

2. The cell suction system according to claim 1, wherein the microscope is arranged such that both of an optical input signal and the optical output signal are introduced into and removed from the light path connecting the objective lens and the imaging lens, through the imaging lens, further pass through the container, and reach the front end part of the tubular tip.

3. The cell suction system according to claim 2, wherein the optical output signal is image information on the front end part of the tubular tip.

4. The cell suction system according to claim 1, wherein the microscope is arranged such that both of an optical input signal and the optical output signal are introduced into and removed from a portion in the middle of the light path connecting the objective lens and the imaging lens, further pass through the container, and reach the front end part of the tubular tip.

5. The cell suction system according to claim 4, wherein the optical output signal is reflective information on the front end part of the tubular tip.

6. The cell suction system according to claim 5, wherein the optical output signal is acquired by a confocal point optical type.

7. The cell suction system according to claim 5, wherein the optical output signal is acquired by an astigmatic type.

8. The cell suction system according to claim 5, wherein the optical output signal is acquired by a knife edge type.

9. The cell suction system according to claim 5, wherein the optical output signal is acquired by an image contrast type.

10. The cell suction system according to claim 1, wherein the optical output signal is image information on the front end part of the tubular tip, and
wherein the processor is configured to execute the instructions to detect a position in a height direction where the image information of the highest contrast is obtained when the front end part of the tubular tip is moved in the longitudinal direction as the position where the front end part of the tubular tip is located at the focal point of the objective lens.

11. The cell suction system according to claim 1, wherein the optical output signal is reflective information on the front end part of the tubular tip, and
wherein the processor is configured to execute the instructions to detect a position in a height direction where the highest quantity of reflected light included in the reflective information is obtained when the front end part of the tubular tip is moved in the longitudinal direction as the position where the front end part of the tubular tip is located at the focal point of the objective lens.

12. The cell suction system according to claim 1, wherein the imaging lens is arranged on a rear aperture side of the objective lens.

13. A method for performing suction work of a substance within a cell using a cell suction system according to claim 1, the method comprising:
suctioning, by the tubular tip, the substance from the inside of the cell received in the container;
detecting, by the detection section, the position of the front end part of the tubular tip; and
moving the tubular tip to guide the front end part of the tubular tip into one specific cell based on the output signal obtained in the detection section.

14. The method according to claim 13, wherein the microscope is arranged such that both of an optical input signal and the optical output signal are introduced into and removed from the light path connecting the objective lens and the imaging lens, through the imaging lens, further pass through the container, and reach the front end part of the tubular tip.

15. The method according to claim 14, wherein the optical output signal is image information on the front end part of the tubular tip.

16. The method according to claim 13, wherein the microscope is arranged such that both of an optical input signal and the optical output signal are introduced into and removed from a portion in the middle of the light path connecting the objective lens and the imaging lens, further pass through the container, and reach the front end part of the tubular tip.

17. The method according to claim 16, wherein the optical output signal is reflective information on the front end part of the tubular tip.

18. The method according to claim 17, wherein the optical output signal is acquired by a confocal point optical type.

19. The method according to claim 17, wherein the optical output signal is acquired by an astigmatic type.

20. A cell suction system that supports suction work of a substance within a cell, the cell suction system comprising:
a container configured to receive the cell;
a tubular tip configured to suction the substance from the inside of the cell received in the container;
a microscope having an objective lens and an imaging lens, the objective lens being arranged below the container and at a height that is as close to the container; and
a detection section configured to detect a position of a front end part of the tubular tip, the detection section comprising:
an optical component assembly comprising:
a dichroic mirror configured to reflect at least a portion of light having passed through the objective lens and entering into the dichroic mirror;
a condensing lens configured to condense light reflected by the dichroic mirror;
at least one of a pinhole and a knife edge disposed at a focal position of the condensing lens; and
at least one of a light-receiving sensor and a camera configured to detect light having passed through the at least one of the pinhole and the knife edge,
the optical component assembly being configured to acquire an optical output signal of the front end part of the tubular tip from a light path connecting the objective lens and the imaging lens;
at least one memory storing instructions; and
at least one processor coupled to the optical component assembly and programmed to execute the instructions to detect the position of the front end part of the tubular tip based on an optical output signal of the front end part of the tubular tip acquired from a light path connecting the objective lens and the imaging lens,
wherein a direction of an optical axis of the objective lens and a longitudinal direction including the front end part of the tubular tip are parallel, and wherein the processor is programmed to execute the instructions to detect a position in a height direction where the front end part of the tubular tip is located at a focal point of the objective lens based on variation of the output signal when the front end part of the tubular tip is moved in the longitudinal direction, the processor determines that the front end part of the tubular tip is located at the focal point of the objective lens when the optical output signal of the front end part of the tubular tip indicates that the light-receiving sensor receives a highest quantity of light having passed through the at least one of the pinhole and the knife edge, or when a contrast of the front end part of the tubular tip is highest in the optical output signal of the front end part of the tubular tip acquired by the camera.

21. A cell suction system that supports suction work of a substance within a cell, the cell suction system comprising:
a container configured to receive the cell;
a tubular tip configured to suction the substance from the inside of the cell received in the container;
a microscope having an objective lens and an imaging lens, the objective lens being arranged below the container and at a height that is as close to the container; and
a detection section configured to detect a position of a front end part of the tubular tip, the detection section comprising:
an optical component assembly comprising:
a dichroic mirror configured to reflect at least a portion of light having passed through the objective lens and entering into the dichroic mirror;
a cylindrical lens configured to condense light reflected by the dichroic mirror into a line; and
a quadrant light-receiving sensor configured to detect, with at least four areas thereof, light having passed through the cylindrical lens,
the optical component assembly being configured to acquire an optical output signal of the front end part of the tubular tip from a light path connecting the objective lens and the imaging lens;
at least one memory storing instructions; and
at least one processor coupled to the optical component assembly and programmed to execute the instructions to detect the position of the front end part of the tubular tip based on an optical output signal of the front end part of the tubular tip acquired from a light path connecting the objective lens and the imaging lens,
wherein a direction of an optical axis of the objective lens and a longitudinal direction including the front end part of the tubular tip are parallel, and
wherein the processor is programmed to execute the instructions to detect a position in a height direction where the front end part of the tubular tip is located at a focal point of the objective lens based on variation of the output signal when the front end part of the tubular tip is moved in the longitudinal direction, the processor determines that the front end part of the tubular tip is located at the focal point of the objective lens when the optical output signal of the front end part of the tubular tip indicates that the quadrant light-receiving sensor detects a zero crossing point.

22. A cell suction system that supports suction work of a substance within a cell, the cell suction system comprising:
a container configured to receive the cell;
a tubular tip configured to suction the substance from the inside of the cell received in the container; and
a detection section configured to detect a position of a front end part of the tubular tip, the detection section comprising:
an optical component assembly comprising:
a pinhole array disk comprising a plurality of pinholes and configured to rotate;
a dichroic mirror configured to reflect at least a portion of light having passed through the objective lens and the pinhole array disk and entering into the dichroic mirror;
a filter wheel comprising a plurality of band-pass filters and a through position formed with a vacant hole at which no band-pass filter is mounted, the filter wheel being configured to either limit a passband of light reflected by the dichroic mirror with one of the band-pass filters or not limit the passband of the light reflected by the dichroic mirror at the through position; and
a camera configured to detect the light reflected by the filter wheel,
the optical component assembly being configured to acquire an optical output signal of the front end part of the tubular tip from a light path connecting the objective lens and the imaging lens;
at least one memory storing instructions; and
at least one processor coupled to the optical component assembly and programmed to execute the instructions to detect the position of the front end part of the tubular tip based on an optical output signal of the front end part of the tubular tip acquired from a light path connecting the objective lens and the imaging lens,
wherein a direction of an optical axis of the objective lens and a longitudinal direction including the front end part of the tubular tip are parallel, and
wherein the processor is programmed to execute the instructions to detect a position in a height direction where the front end part of the tubular tip is located at a focal point of the objective lens based on variation of the output signal when the front end part of the tubular tip is moved in the longitudinal direction,
the processor determines that the front end part of the tubular tip is located at the focal point of the objective lens when a contrast of the front end part of the tubular tip is high in the optical output signal of the front end part of the tubular tip.

* * * * *